United States Patent [19]
Haindl

[11] Patent Number: 5,464,398
[45] Date of Patent: Nov. 7, 1995

[54] CATHETER

[76] Inventor: Hans Haindl, 3015, Wennigsen 1, Germany

[21] Appl. No.: 66,142
[22] PCT Filed: Apr. 11, 1991
[86] PCT No.: PCT/EP91/02071
  § 371 Date: Jul. 23, 1993
  § 102(e) Date: Jul. 23, 1993
[87] PCT Pub. No.: WO92/09326
  PCT Pub. Date: Jun. 11, 1992

[30] Foreign Application Priority Data

Nov. 27, 1990 [DE] Germany ............ 40 37 641.9

[51] Int. Cl.⁶ .................. A61M 25/00; A61M 3/00
[52] U.S. Cl. ................................ 604/280; 604/43
[58] Field of Search .................. 604/43, 96, 101, 604/102, 280; 128/207.15; 606/192, 194

[56] References Cited

U.S. PATENT DOCUMENTS

| | | | |
|---|---|---|---|
| 1,696,018 | 12/1928 | Schellberg | 604/280 |
| 4,072,146 | 2/1978 | Howes. | |
| 4,141,364 | 2/1979 | Schultze | 604/96 |
| 4,240,433 | 12/1980 | Bordow | 604/96 |
| 4,406,656 | 9/1983 | Hattler et al. | 604/280 |
| 4,601,713 | 7/1986 | Fuqua | 604/280 |
| 4,705,501 | 11/1987 | Wigness et al. | 604/43 |
| 4,932,959 | 6/1990 | Horzewski | 604/165 |
| 4,955,375 | 9/1990 | Martinez | 604/43 |
| 5,106,368 | 4/1992 | Uldall et al. | 604/43 |
| 5,342,350 | 8/1994 | Amiel | 604/96 |

FOREIGN PATENT DOCUMENTS

| | | |
|---|---|---|
| 1219785 | 3/1987 | Canada. |
| 0386408 | 9/1990 | European Pat. Off.. |
| 3035243C2 | 12/1982 | Germany. |
| WO86/07267 | 12/1986 | WIPO. |
| WO88/10128 | 12/1988 | WIPO. |

OTHER PUBLICATIONS

Publication B. Braun–Certofix Duo/Trio (2 pages).
Publication Medical Components Inc. (Cover sheet, pp. 4 and 6).

Primary Examiner—C. Fred Rosenbaum
Assistant Examiner—Frank Wilkens, III
Attorney, Agent, or Firm—Banner & Allegretti, Ltd.

[57] ABSTRACT

A catheter (1, 18) is essentially rigid in cross-section in the peripheral region, and has at least two lumina (3, 4, 19, 20), which are mutually separated by a wall (2, 21) which can be expanded and/or deformed in the transverse plane. The flow cross-sections of the lumina change owing to the deformation of the separating wall (2, 21), depending on the prevailing differential pressure. If drugs are introduced through the lumina one after another, then there is used, in the lumen, an over pressure in relation to the other lumen or lumina, which causes a deformation of the separating wall (2, 21), and hence a reduction in the resistance to flow. The catheter (24) can, therefore, be given a smaller cross-section than that of the prior art multi-lumen catheters (32, 33, 34), resulting in easier manipulation by the doctor and less risk for the patient.

12 Claims, 2 Drawing Sheets

CATHETER

BACKGROUND OF THE INVENTION

The invention relates to a multi-lumen catheter and more particularly, to a multi-lumen catheter having a deformable separating wall between adjacent lumina.

A double-lumen catheter, which consists of a tube which is rigid in its cross-section, in which an additional thinner tube, with a rigid cross-section, proceeds in a "side by side" manner, which tube is firmly connected with the internal wall of the outer tube, is already known from the publication "Medcomp" of the firm Medical Components, Inc., of 14999 Delp Drive, Harleysville, Pa. 19438, U.S.A., page 4. One lumen is formed between the inner and the outer tube, while the second lumen is formed within the inner tube. An additional double-lumen catheter, which is constructed on the basis of the same principle as the first-described catheter, but in which the inner tube proceeds loosely and coaxially in the outer tube, however, is also depicted and described on page 6 of the said "Medcomp" publication.

Catheters of the type under discussion, which consist of a tube which is flexible over its length, but is, however, essentially rigid in its cross-section, and which proceed in three independent lumina, are already known from the publication WO 8810128-A, as well as through the publication "CERTOFIX DUO/TRIO" of the firm B. Braun, of Melsungen AG in D-3508, Melsungen.

There is a strong need, within the field of medicine, for multi-lumen catheters in order to be able to introduce incompatible medications through a single catheter separately from one another, and also, furthermore, in order to make a parallel infusion possible, both by means of gravity, as well as by means of a pump. All of the catheters described above have a relatively large diameter, since their total cross-section essentially corresponds to the sum of the individual cross-sections of the individual lumina. Because of the greater cross-section as well as the cross-pieces separating the individual lumina from one another within the interior of the catheter, a greater rigidity also arises, because of the increased resistance moment. There additionally exists the disadvantage that the stiffening which is brought about from the cross-pieces between the lumina negatively influences the bending behavior of the catheter, at least in a number of directions of bending. For this reason, the wall thicknesses of such multi-lumen catheters must be greater than is the case with single-lumen catheters. In addition, the flow resistance is increased in the lumina, since the wall surface is increased relative to a round, single-lumen catheter. This applies, in particular, for the known catheters which have been described above, in which the lumen, which is formed between the inner and the outer tube, has a disproportionately large circumferential surface. Flow resistance is, as is known, essentially determined by the size of the circumferential surface.

One additional disadvantage of the multi-lumen catheter described above consists of the fact that, as statistics show, the risk to patients is increased with their use. The large diameter, which makes a relatively larger puncture necessary, and which, within a vessel, constricts the cross-section of the same, is, above all, responsible for this. In addition, because of the increased bending stiffness, bending forces are conveyed to the puncture opening and to the vessel to a greater extent.

The task which forms the basis of the invention is that of creating a catheter of the type under discussion which has at least two lumina, the cross-sections of which are reduced in relation to the known types of multi-lumen catheters, and the bending resistance of which is reduced, and in which, furthermore, the risk for the patients is reduced.

The task which forms the basis of the invention is solved by means a multi-lumen catheter incorporating a separating wall between lumina that is deformable.

The invention is based on the basic idea that the individual lumina of a multi-lumen catheter are not, or must not, be simultaneously used with their full through-flow capacity. Within a circumferential area which is essentially rigid in its cross-section, and which, as is the case with a one-lumen, tube-shaped catheter, ensures the desired handling, the cross-section of the single-lumen is variable. This is brought about through the fact that the separating wall between both of the lumina is expansible and/or deformable within the transverse plane. By this means, it is possible to increase the cross-section within a lumen, by means of pressure, which is increased relative to the other lumen or to the other lumina, at the expense of the other lumen or the other lumina. The same then applies for the other lumen, or for the other lumina. In a three-lumen catheter, additional possibilities result in which, for example, two lumina can increase their cross-section at the expense of the third lumen, or vice versa. In catheters with still more lumina, additional possibilities for variation result.

Because of their expandability and/or deformability, the separating walls either do not increase the resistance moment of the entire catheter, or else they only do so to a non-significant extent. By this means, the characteristics and the manipulation relative to the simplest and most favorable form of a catheter—that is to say, of a tube—remain practically unchanged. The manipulation is correspondingly simple for the physician, and the risk for the patient is slight.

The inner separating wall between the individual lumina can have any desired form of implementation. In one embodiment, the separating wall forms an internal tube which proceeds within an external tube, which forms the circumferential area of the catheter which is essentially rigid in its cross-section. If the lumen is stressed, by means of a fluid with pressure, between the internal tube and the external tube, then the internal, deformable and flexible tube collapses, either in part or in whole, so that the lumen extends, between the internal tube and the external tube, over practically the entire internal width of the external tube. If the internal tube is stressed with a fluid which is under pressure which is greater than the pressure between the internal tube and the external tube, then the internal tube expands over its entire cross-section. If the internal tube is not only flexible—which is the case in a thin, but tension-proof material—but also expandable, then, under the corresponding pressure stressing of the internal tube, its cross-section can expand to the internal cross-section of the external tube. In this case, the entire internal cross-section of the external tube is, in an extreme case, available for both of the variable lumina.

In the embodiment stated above, the internal tube can proceed loosely in the external tube. The internal tube can, however, also be partially connected with the external tube. Several internal tubes can also proceed simultaneously within the external tube.

In another form of implementation of the basic idea in accordance with the invention, the separating wall extends diametrically or as secant, in an essentially round tube forming the circumferential area which is rigid in its cross-section, and is longer than the diameter or the secant. This essentially applies for the event that the cross-piece is less expandable than it is deformable. Since it is longer than the diameter or the secant, it assumes, if no pressure is applied, any form which is desired, such as, for example, a coiled or arced shape. Upon application of pressure in one lumen (or with an increased pressure relative to the other lumen), the cross-piece deforms in the sense of an enlargement of the pressure-stressed lumen and assumes—in the extreme case—depending on its length, a shape in which it is applied to the internal wall of the external tube, so that the lumen which is not stressed with pressure is, consequently, essentially made to disappear.

In yet another form of implementation of the present invention the separating wall has at least three partial separating walls, which proceed together in a star-like shape, and thus form at least three lumina. If the partial separating walls are thereby extended, then they should consist of an expandable material. It is appropriate, however, if they are, in a manner similar to the above-stated form of implementation, longer than the direct connecting line between their common, central connecting point and the connecting point on the external circumference. Without a pressure stressing, they all proceed in an arc-shaped manner, for example, or else the arc which is either without pressure, or which is under the lower pressure, can, under the influence of the lumen which has the greater pressure stressing on it, bend outwardly.

The distal end of the catheter can essentially be constructed in any form which is desired. In the form of implementation in which the separating wall forms an internal tube, this is connected, at the distal end of the catheter, suitably tightly joined with the preferably thinned external end of the outer tube, and an aperture is located in the external tube and at a distance from the distal end. In this manner, the distal apertures of both of the lumina replaced at a distance from one another, which is particularly appropriate for incompatible drugs.

In the forms of implementation, in which the separating wall proceeds diametrically or as a secant, or in which the separating walls proceed essentially radially, it is appropriate that the lumina arc, in the distal end of the catheter, sealed into one, while the sealed lumen, or the sealed lumina, have, at a distance from the distal end of the catheter, preferably at different distances from the same, through-flow apertures through the external circumferential area which is rigid in its cross-section. Even in the case of several lumina, therefore, a separation of the distal opening apertures is possible, in order to thereby be able to spatially separate non-compatible drugs from one another.

For the purpose of the connection of the proximal end of the catheter in accordance with the invention, it is appropriate if the lumina are expanded in their diameter at the proximal end of the catheter, and are provided, within this area, with a connecting piece for the connection of the lumina. In this manner, the lumina are not adversely affected in their diameter by the connecting piece. The expansion of the diameter is suitably brought about by means of an interval extrusion, or by means of the expansion of a heated tool.

For the connection of a catheter in accordance with the invention, in which the separating wall forms a tube in an external tube, it is appropriate that, on the proximal end, the internal tube projects beyond the external tube. Both ends of the tubes are tightly inserted into coaxial recesses of an attachment piece whereby, behind each end of the tubes, a space which can be connected with a connection, or which is connected with a connection, is located.

BRIEF DESCRIPTION OF THE DRAWING.

The examples of implementation will be illustrated in greater detail by means of the attached drawing, wherein like numerals refer to like elements in the various views and wherein.

DETAILED DESCRIPTION OF THE PRESENT INVENTION

Figure 1:
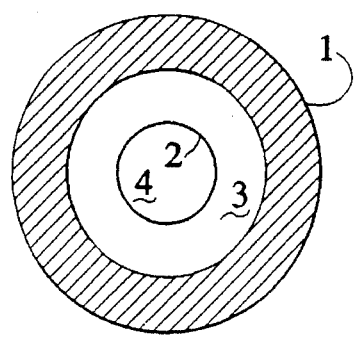
FIG. 1 depicts a first form of implementation of the invention.

FIG. 1 depicts, in a cross-section, a catheter which consists of an external tube 1 as well as an internal tube 2. Between the tubes I and 2, there is a lumen 3 and, within the interior of the internal tube 2, another lumen 4 is formed. The external tube has a relatively great wall thickness and is, like the conventional tube catheters, essentially rigid in its cross-section, but is, however, flexible over its longitudinal expansion. The internal tube 2 has a very slight wall thickness and is, therefore, very easy to deform.

If, during the use of a catheter in accordance with FIG. 1, the lumen 3 is stressed with a fluid under pressure, while the lumen 4 is stressed with a pressure which is smaller, or with no pressure, then the thin, internal tube 2 collapses. It can, in the extreme case, collapse entirely, so that the lumen 3 expands into the entire internal cross-section of the external tube 1. If the lumen 4 is, after that, stressed with pressure, while the lumen 3 is stressed with a smaller pressure, or with no pressure, then the internal tube 2 again expands to its complete circumference, so that the lumen 4 again has full size. If the wall of the internal tube 2 is expandable then, in the event of corresponding pressure in the lumen 4, this can expand still further at the expense of the lumen 3, and it is even possible for the tube 2 to expand so far that it is applied, over the entire circumference, to the internal wall of the external tube 1. The lumen 4 has, in this case, the same cross-section as the lumen 3 has in the case stated above. The lumina 3 and 4 can, therefore, alternately occupy the entire internal cross-section of the external tube 2.

Figure 2:
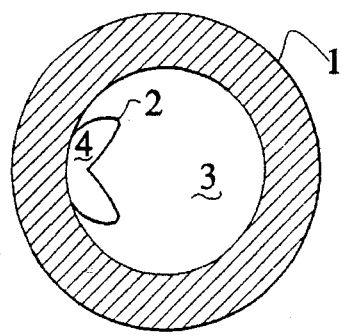
FIG. 2 depicts a form of implementation which is modified relative to the form of implementation in accordance with FIG. 1.

FIG. 2 depicts, in a cross-section, one form of implementation in accordance with FIG. 1. Equivalent parts are provided with the same reference figures. The difference consists of the fact that the tube 2 is attached, over a portion of its circumference, to an internal wall 5 of the external tube 1. It thereby has a thoroughly defined position within the external tube 1. In the position which is depicted in FIG. 2, the wall of the internal tube 2 is bent somewhat inwardly. This can be the resting position, but it can also result if the lumen 3 is stressed under pressure.

Figure 3:
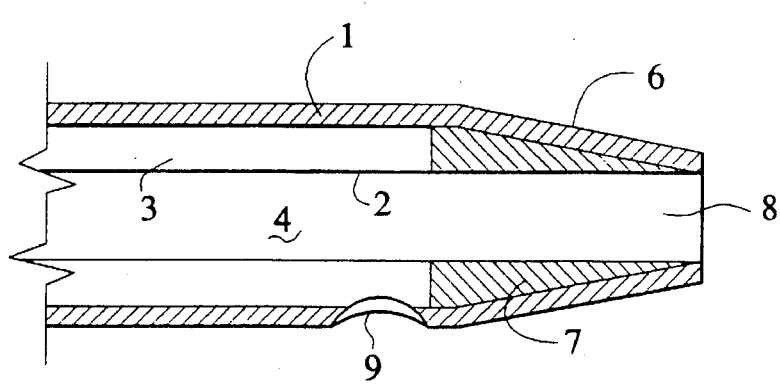
FIG. 3 depicts, in a longitudinal section, the construction of the distal end of the catheter in accordance with FIG. 1.

FIG. 3 depicts, in a longitudinal section, a distal end of the catheter in accordance with FIG. 1. The external tube 1 has a conical tapering 6 up to a diameter corresponding to the external diameter of the internal tube 2, in the area of which the inner tube 2 is connected—by means of material 7, such as adhesive or a hardening plastic, for example—with the external tube 1. At a distance from one opening 8 of the internal tube 2, a through-flow aperture 9 is located, behind the material 7, within the external tube 1.

Figure 4:
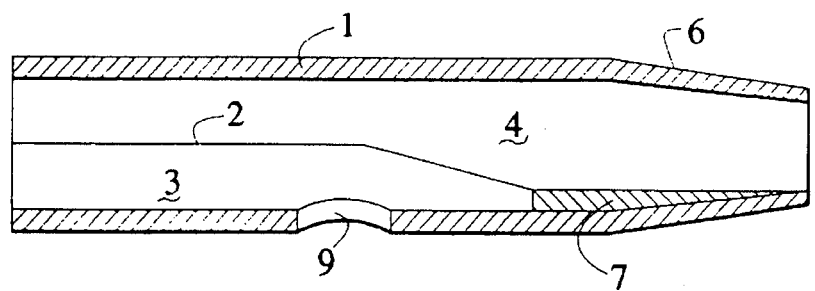
FIG. 4 depicts, in a longitudinal section, the construction of the distal end of the catheter in accordance with FIG. 2.

FIG. 4 depicts a distal end of a catheter, in accordance with FIG. 2, similar to that in FIG. 3. The same or corresponding parts are provided with the same reference numbers. The difference consists of the fact that the internal tube 2 does not proceed coaxially as it does in FIG. 3, but is, rather, attached to the internal wall 5 of the external tube 1.

Figure 5:
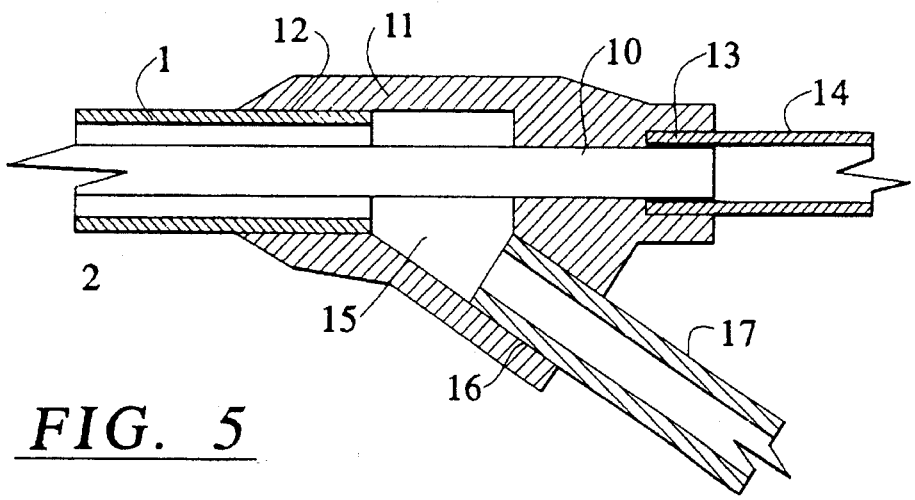
FIG. 5 depicts, in a cross-section, the proximal end of the catheter in accordance with FIG. 1.

FIG. 5 depicts, in a longitudinal section, the construction of the proximal end of the catheter in accordance with FIG. 1. The internal tube 2 projects over the external tube 1 and fits tightly within a recess 10 of a connecting piece 11, in which, in addition, an additional recess 12 is located, coaxially to the recess 10, in which the external tube 1 tightly fits. The recess 10 has an expansion 13, into which one end of the connecting tube 14 is placed, and is tightly connected with the rear end of the internal tube 2.

In the area between the recesses 10 and 12, there is positioned, within the connecting piece 11, an annular space 15 which discharges into a recess 16, into which a connecting tube 17 is tightly inserted.

Figure 6:
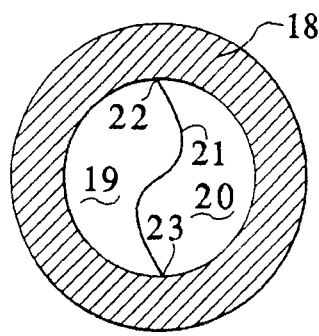
FIG. 6 depicts, in a cross-section, a third form of implementation of the catheter, without the application of pressure.
Figure 7:
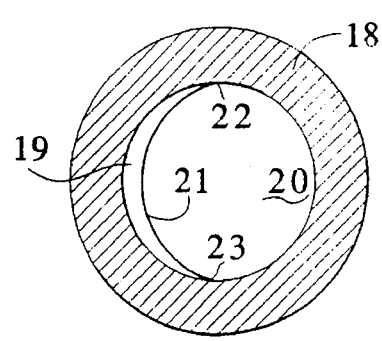
FIG. 7 depicts, in a cross-section, the catheter in accordance with FIG. 6, with pressure stressing a lumen.

FIG. 6 depicts, in section, one form of implementation with an external circumferential area 18, which is rigid in its cross-section, which is essentially tube-shaped, and within which two lumina 19 and 20 are located, which are separated by means of a separating wall 21, which extends between two diametrically opposed points 22 and 23. In the depiction in FIG. 6, both of the lumina 19 and 20 are stressed with the same pressure, or with no pressure. The cross-piece 21 has an "S"-shape and is, therefore, longer than the diametrical distance between the points 22 and 23. The separating wall is slightly deformable. Under the pressure stressing of the lumen 20, for example, the separating wall 21 expands outwardly in the sense of an enlargement of the lumen 20, and assumes the shape which is evident from FIG. 7. It can be seen that the lumen 20 is significantly expanded, in its cross-section, relative to the lumen 19. If the pressure within the lumen 19 is greater relative to that in the lumen 20, then the ratios are, of course, reversed.

Figure 8:
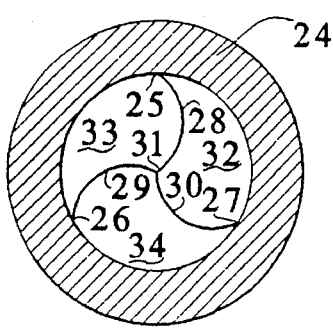
FIG. 8 depicts, in a cross-section, a fourth form of implementation of the invention, without the application of pressure.

FIG. 8 depicts, in a cross-section, one example of implementation similar to that of FIG. 6. A circumferential area 24 has the form of a tube which is rigid in its cross-section, in which the separating walls 30 which are deformable in a star-shape or proceeding radially outwardly from points 25, 26 and 27 which proceed closely together in a point 31. In this manner, lumina 32, 33 and 34 are formed.

In the position which is depicted in FIG. 8, there is either no pressure in the lumina 32, 33 and 34, or else there is equal pressure. The separating walls 28, 29 and 30 thereby proceed in an arc-like manner, but can also, however, occupy another desired form, depending on their deformability. In every case, they are longer than the radial distance between the point 31 and the specific points 25, 26 and 27.

Figure 9:
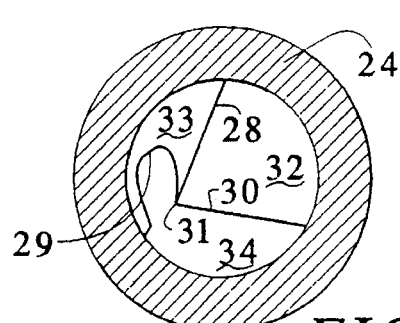
FIG. 9 depicts, in a cross-section, the form of implementation in accordance with FIG. 8, with pressure stressing a lumen.

If the lumen 32 is stressed with a pressure, while the lumina 33 and 34 are stressed with only slight pressure, or with no pressure, then the separating walls 28 and 30 extend, as is depicted in FIG. 9, while the separating wall 29 collapses. By this means, the lumen 32 expands, while the lumina 33 and 34 contract. Depending on the level of the pressure in the lumen 32, it is also possible for the separating walls 28 and 30 to curve by way of an enlargement of the lumen 32, that is to say, away from the lumen 32, as is indicated by means of the dotted lines 28' and 30'.

If the pressure is greater in one of the other lumina 32, 34, then corresponding ratios result.

Figure 10:
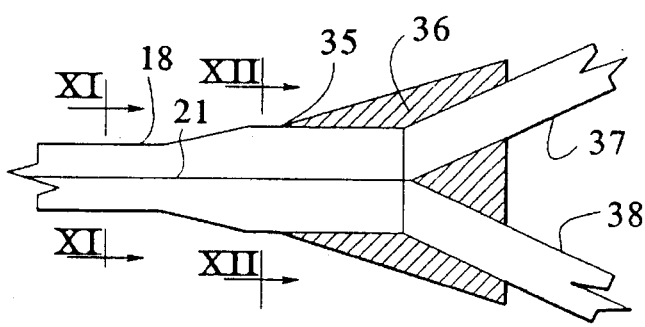
FIG. 10 depicts, in the longitudinal section, the construction of the proximal end of the catheter in accordance with FIG. 6.
Figures 11, 12:
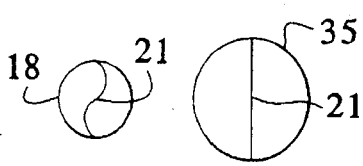
FIG. 11 is a cross-section taken generally along line of "XI—XI", of FIG. 10.
FIG. 12 is a cross-section taken generally along line "XII—XII" FIG. 10.

FIG. 10 depicts the proximal end of the catheter in accordance with FIG. 6 in the longitudinal section; FIG. 11 is a cross-section taken along line "XI—XI" through FIG. 10. FIG. 12 is a cross-section taken along line "XII—XII", through FIG. 10. It is clear, from all three FIGS. 10, 11 and 12, that the cross-section of the catheter is expanded in the area of one end 35 and sits tightly in a connecting piece 36, which produces the connection with the two connecting tubes 37 and 38. The distal end of the catheter can be constructed in precisely the manner which is depicted in FIG. 4.

Figure 13:
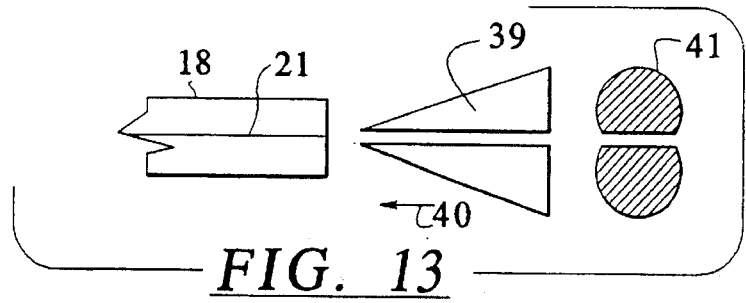
FIG. 13 is a cross sectional view of the production tools.

FIG. 13 clarifies the production of the expanded end 35 through the introduction of a warm, wedge-shaped tool 39 in the direction of the arrow 40. A cross-section 41 of the tools is depicted to the right in FIG. 13.

I claim:

1. A catheter comprises an external tube which has a relatively thick wall and which is in part, essentially rigid in cross-section, and which comprises at least two lumina which are separated from one another by a separating wall, characterized in that the catheter in its circumferential area is rigid but is flexible over its length, and, the separating wall is relatively thin and is very easy to deform and move in a direction transverse to the length of the catheter, and that said lumina are each open at both ends.

2. A catheter in accordance with claim 1, characterized in that, the separating wall forms an internal tube, which is disposed inside an external tube which forms the circumferential area of the catheter which is essentially rigid in its cross-section.

3. A catheter in accordance with claim 2, characterized in that, the internal tube is disposed loosely in the external tube.

4. A catheter in accordance with claim 2, characterized in that, the internal tube is connected, over a portion of its circumference, with the external tube.

5. A catheter in accordance with claim 2, characterized in that, several internal tubes are positioned in the external tube.

6. A catheter in accordance with claim 1, characterized in that, said separating wall is disposed in an essentially round tube forming said circumferential area which is rigid in cross-section, and which is longer than said cross-section.

7. A catheter in accordance with claim 6, characterized in that, the separating wall is long enough that it can be applied to the one side or the other up to an adjacent internal wall of a lumen.

8. A catheter in accordance with claim 1, characterized in that, the separating wall has at least three partial separating walls which proceed in a star-like pattern to one another, and thus form at least three lumina.

9. A catheter in accordance with claim 2, characterized in that, the internal tube is tightly connected, on the distal end of the catheter, with an external end of the external tube, being tapered preferably having a tapering, and that, a through-flow aperture is located, within the external tube, at a distance from the distal end.

10. A catheter in accordance with claim 6 or 8, characterized in that, the lumina on the distal end of the catheter are sealed into one, and that the sealed lumen or the sealed lumina has, or have, at a distance from the distal end of the catheter preferably at different distances from the same, through-flow apertures which proceed through the external circumferential area.

11. A catheter in accordance with claim 1, characterized in that, the lumina at the proximal end of the catheter are enlarged, and are provided, in this area, with a connecting piece for the connection of the lumina.

12. A catheter in accordance with claim 2, characterized in that, at the proximal end of the catheter, the internal tube projects beyond the external tube; and, both ends of the tubes are tightly received in coaxial recesses of a connecting piece, whereby an annular space is located, behind each of the ends of the tubes, said space being operatively connected to a connection.

* * * * *